United States Patent
Fox et al.

[11] Patent Number: 5,827,214
[45] Date of Patent: Oct. 27, 1998

[54] TAMPON APPLICATOR

[75] Inventors: Donald George Fox, Neenah; Tammy Jo Rentmeester, Appleton; Steven James Nielsen, Greenville, all of Wis.

[73] Assignee: Kimberly-Clark Worldwide, Inc., Neenah, Wis.

[21] Appl. No.: 949,075

[22] Filed: Oct. 10, 1997

Related U.S. Application Data

[63] Continuation of Ser. No. 582,241, Jan. 3, 1996, abandoned, which is a continuation of Ser. No. 294,169, Aug. 22, 1994, abandoned.

[51] Int. Cl.[6] ........................................... A61F 13/20
[52] U.S. Cl. ....................................... 604/14; 604/15
[58] Field of Search ................................. 604/11, 14, 15, 604/16, 904

[56] References Cited

U.S. PATENT DOCUMENTS

| | | |
|---|---|---|
| 2,413,480 | 12/1946 | Winter . |
| 2,639,646 | 5/1953 | Thompson et al. . |
| 2,922,422 | 1/1960 | Bletzinger . |
| 2,922,423 | 1/1960 | Rickard et al. . |
| 3,204,635 | 9/1965 | Voss et al. . |
| 3,433,225 | 3/1969 | Voss et al. . |
| 3,499,447 | 3/1970 | Mattes et al. . |
| 3,581,744 | 6/1971 | Voss et al. . |
| 3,674,026 | 7/1972 | Werner et al. . |
| 3,753,437 | 8/1973 | Hood et al. . |
| 3,760,808 | 9/1973 | Bleuer . |
| 3,764,438 | 10/1973 | Voss et al. . |
| 4,312,348 | 1/1982 | Friese . |
| 4,412,833 | 11/1983 | Wiegner et al. ................ 604/14 |
| 4,413,986 | 11/1983 | Jacobs ........................... 604/14 |
| 4,508,531 | 4/1985 | Whitehead ..................... 604/14 |
| 4,573,963 | 3/1986 | Sheldon ......................... 604/15 |
| 4,610,659 | 9/1986 | Friese ............................ 604/11 |
| 4,726,805 | 2/1988 | Sanders, III .................... 604/15 |
| 4,960,417 | 10/1990 | Tarr, Jr. et al. ................. 604/15 |
| 5,080,659 | 1/1992 | Nakanishi ...................... 604/904 |
| 5,087,239 | 2/1992 | Beastall et al. ................. 604/14 |
| 5,153,971 | 10/1992 | Van Iten ......................... 28/118 |
| 5,158,535 | 10/1992 | Paul et al. ...................... 604/15 |
| 5,330,421 | 7/1994 | Tarr et al. ...................... 604/18 |
| 5,370,633 | 12/1994 | Villalta ........................ 604/385.1 |
| 5,389,067 | 2/1995 | Rejai ............................. 604/14 |
| 5,569,177 | 10/1996 | Fox et al. ....................... 604/15 |
| 5,601,530 | 2/1997 | Nielsen et al. ................. 604/11 |
| 5,681,894 | 10/1997 | Williams et al. ............... 604/11 |
| 5,693,009 | 12/1997 | Fox et al. ....................... 604/14 |

FOREIGN PATENT DOCUMENTS

| | | |
|---|---|---|
| 0146320 | 6/1985 | European Pat. Off. ........ 604/904 |
| 0221424 | 5/1987 | European Pat. Off. . |
| 0243250 | 10/1987 | European Pat. Off. . |
| 2153684 | 8/1985 | United Kingdom ........... 604/904 |

*Primary Examiner*—Mark O. Polutta
*Attorney, Agent, or Firm*—Thomas J. Connelly

[57] ABSTRACT

A tampon applicator is disclosed which includes first and second telescopically assembled members. The first member is designed to house an absorbent tampon. The first member has first and second spaced apart ends and is formed from at least two separate and distinct layers. An insertion tip is integrally formed on the first end of the first member and extends outwardly therefrom. The insertion tip is constructed from at least one of the two distinct layers and has a thickness which is less than that of the first member. The second member is telescopically mounted in the second end of the first member and is adapted to expel the tampon through the insertion tip as it is pushed into the first member.

17 Claims, 3 Drawing Sheets

TAMPON APPLICATOR

This application is a continuation of application Ser. No. 08/582,241 entitled "TAMPON APPLICATOR" and filed in the U.S. Patent and Trademark Office on Jan. 3, 1996 now abandoned. The entirety of this application is hereby incorporated by reference, which is a continuation of application U.S. Ser. No. 08/294,169 filed Aug. 22, 1994, now abandoned.

FIELD OF THE INVENTION

This invention relates to a tampon applicator having a soft and flexible insertion tip which facilitates placement of a catamenial tampon into a body cavity.

BACKGROUND OF THE INVENTION

Catamenial tampons and other types of absorptive media are routinely inserted into body cavities, such as a woman's vagina, to absorb menstrual fluid, blood and other kinds of body fluid. One convenient way to position such absorbent tampons into a body cavity is through the use of an applicator. Comfortable and clean insertion of the absorbent tampon are keys to repeated purchase of products using such applicators.

Tampon applicators are available in a variety of shapes and sizes with the two piece telescopically assembled design being the most prevalent. In the two piece applicator, the tampon is housed in an outer tube and is expelled into a woman's vagina by an inner member which is telescopically mounted in the outer tube and acts as a plunger. Some tampon applicators utilize a hollow tube having an open insertion end through which the tampon is always exposed while other applicators utilize a completely closed or partially closed design. A thin film membrane can cover the insertion end of an applicator to completely enclose the forward end of a tampon while folds or pleats can be used to partially enclose the forward end of a tampon and protect it from contamination. Still other applicators, especially plastic applicators, have a plurality of flexible petals formed on the forward end of the outer tube which can flex radially outward to allow the tampon to be expelled. It will be appreciated that the diameter of the applicator, the material from which it is formed, the basic configuration of the applicator, the size and shape of the tampon positioned in the applicator, as well as the ease of opening the forward end of the applicator will all influence the force required to expel the tampon therefrom. The expulsion force should be kept reasonably low to permit proper functioning of the applicator.

While many have tried to design and manufacture tampon applicators having these improved qualities, there still remains a need for a tampon applicator which is more comfortable to use. Those applicators having an open forward end tend to expose the dry absorbent fibers of the tampon to the interior walls of a woman's vagina and this can cause irritation during insertion. Commercially available plastic applicators, using a plurality of petal tips separated by slots, can sometimes pinch or cut the vaginal tissue of a woman during insertion and cause discomfort. Paper applicators having partially or fully closed tips tend to require an increased expulsion force to expel the tampon from the applicator and this can cause the applicator to deform or cause the tampon to be inserted incorrectly. Such insertion can cause discomfort to the user.

Now a tampon applicator has been invented having a soft and flexible insertion tip to facilitate placement of a catamenial tampon into a woman's vagina.

SUMMARY OF THE INVENTION

Briefly, this invention relates to a tampon applicator having a soft and flexible insertion tip which facilitates placement of a catamenial tampon into a body cavity. The tampon applicator includes a first member capable of housing an absorbent tampon. The first member has first and second spaced apart ends and is formed with at least two separate and distinct layers. An insertion tip is integrally formed on the first end of the first member and extends outwardly therefrom. The insertion tip is constructed from at least one of the two distinct layers and has a thickness which is less than that of the first member. The tampon applicator also includes a second member telescopically mounted in the second end of the first member. The second member is adapted to expel the tampon through the insertion tip as it is pushed into the first member.

The general object of this invention is to provide a tampon applicator having a soft and flexible insertion tip for facilitating placement of a catamenial tampon into a body cavity. A more specific object of this invention is to provide a tampon applicator having an insertion tip formed from very thin material which substantially encloses the forward end of an absorbent tampon and prevents premature contamination thereof.

Another object of this invention is to provide a tampon applicator having a smooth and soft insertion tip which essentially encloses the forward end of an absorbent tampon and which can be opened with a minimum amount of force.

A further object of this invention is to provide a tampon applicator which is economical to manufacture and easy to use.

Still another object of this invention is to provide a tampon applicator which will minimize discomfort to a woman as she inserts an absorbent tampon into her vagina.

Still further, an object of this invention is to provide a spirally wound, convolutely wound, or longitudinally seamed tampon applicator with a soft and flexible tip for facilitating placement of an absorbent tampon into a woman's vagina.

Other objects and advantages of the present invention will become more apparent to those skilled in the art in view of the following description and the accompanying drawings.

DETAILED DESCRIPTION OF THE PREFERRED EMBODIMENTS

Figure 1:
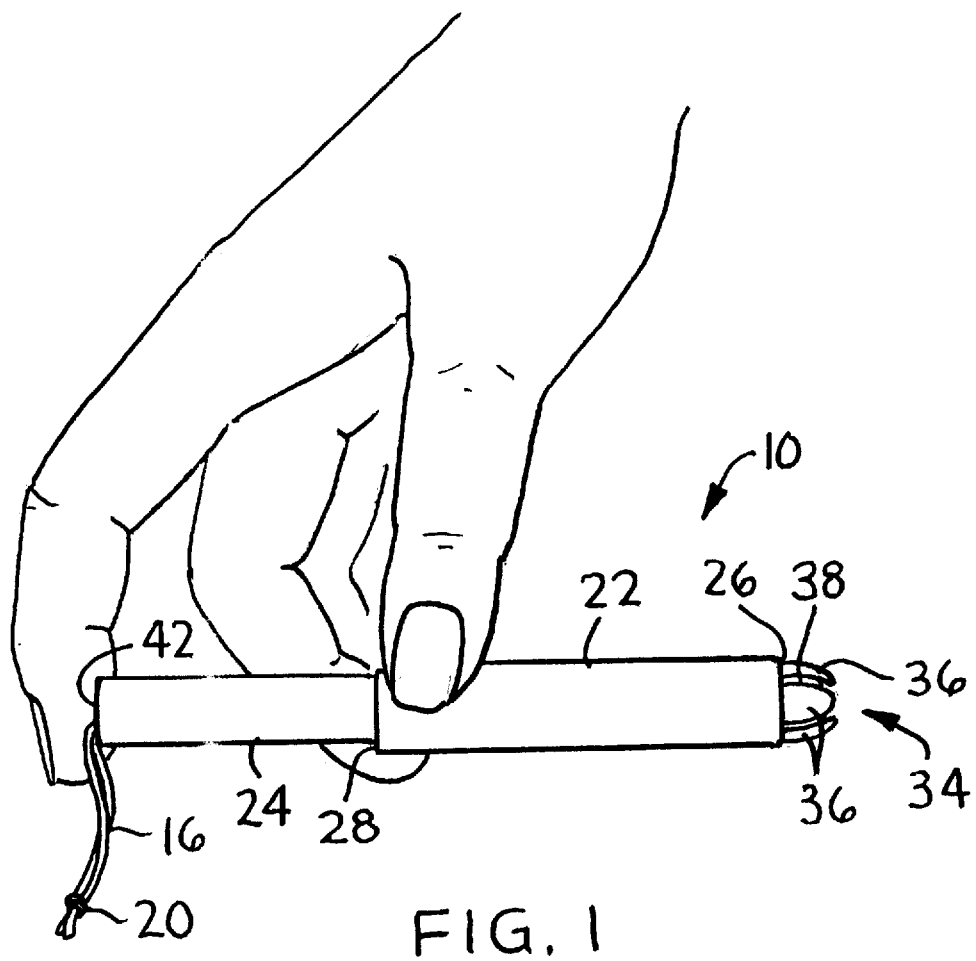
FIG. 1 is a side elevation view of a tampon applicator including an inner tube telescopically mounted in an outer tube and showing a soft and flexible insertion tip formed on the leading end of the outer tube.
Figure 2:
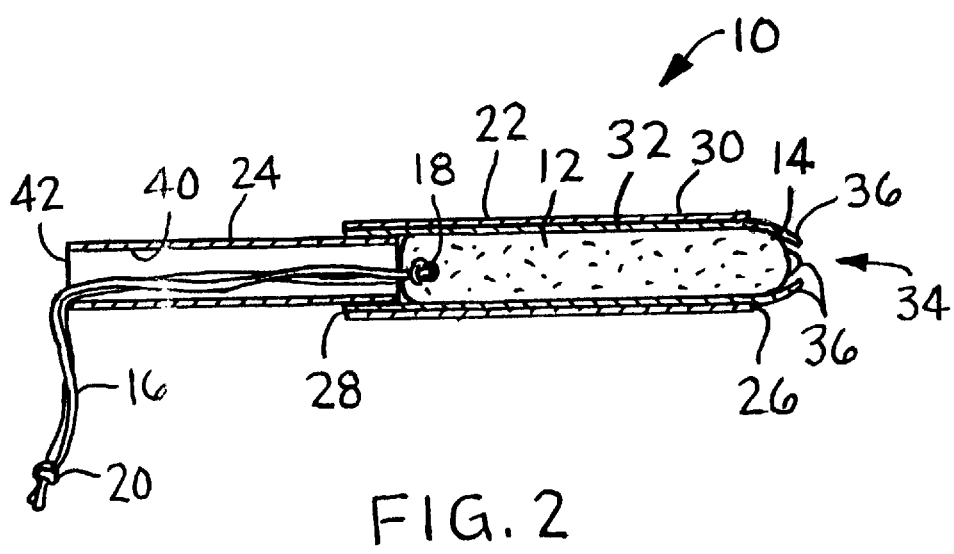
FIG. 2 is a cross-sectional view of the tampon applicator shown in FIG. 1 depicting the presence of a tampon and showing the telescopic assembly of the inner and outer tubes.
Figure 3:
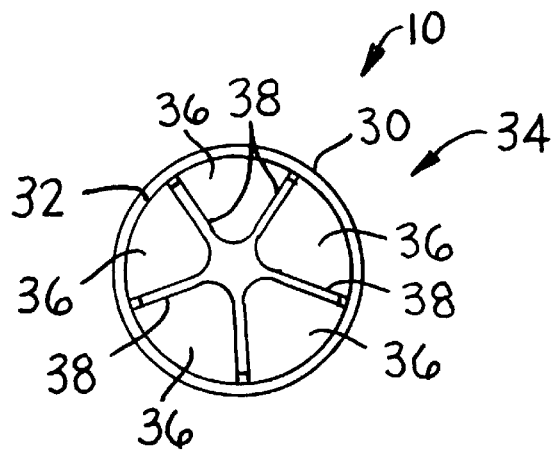
FIG. 3 is a right end view of FIG. 2 showing the insertion tip formed with a plurality of soft and flexible petals.

Referring to FIGS. 1–3, a tampon applicator 10 is shown which is designed to house a catamenial tampon 12 and provide a comfortable means of inserting the tampon 12 into a woman's vagina. A tampon is an absorbent member primarily designed to be worn by a woman during her menstrual period to absorb menses, blood and other body fluid. The tampon 12 can be made from natural or synthetic fibers including cellulose fibers such as cotton or rayon, or artificial fibers such as polyester, polypropylene, nylon or blends thereof. Other types of fibers may also be used, such as cellulose sponge or a sponge formed from elastomeric materials. A blend of cotton and rayon fibers works well.

The tampon 12 is normally compressed into the form of a cylinder and can have a blunt, rounded or shaped forward end 14. The tampon 12 commonly has a withdrawal string 16 fastened to an end thereof which serves as a means for withdrawing the soiled tampon from the woman's vagina. The withdrawal string 16 can be looped through an aperture 18 formed transversely through the tampon 12. In addition, the withdrawal string 16 can have a knot 20 formed at it's free end to assure that the string 16 will not separate from the tampon 12.

The tampon applicator 10 includes a first member 22 and a second member 24. The first member 22, also commonly referred to as an outer tube, is preferably in the form of a hollow tube which is formed from paper, paperboard, cardboard, plastic, thermoplastic film, aqueous coating or a combination thereof. If paper, paperboard or cardboard is used, it can be coated with a wax or water-insoluble polymer to render it water-resistant. Suitable plastic materials include polyolefins, such as low density polyethylene and low density polypropylene. The first member 22 should have sufficient strength and rigidity to prevent collapse under normal vaginal pressures. The first member 22 can also be formed into a cylindrical shape having a longitudinal seam or be spirally or convolutely wound. The first member 22, has a relatively small diameter of about 10 mm to about 20 mm.

The first member 22 has first and second spaced apart ends 26 and 28, respectively. The first member 22 is formed from at least two distinct layers 30 and 32 which may be constructed of equal or different board weight. The first member 22 can be formed from two to eight separate and distinct layers, preferably, from two to five layers, with two or three layers being most preferred. The layers can be made from different materials, for example, paperboard and film, or be made from similar material having different properties, for example, different board weight. It is expected that the exterior layer 30 can be formed from a thin coated paperboard of about 0.06 mm or from a film material having a thickness of about 0.01 mm while one or more inner layers 32 can be formed from a non-coated material having a higher board weight. The exterior layer 30 can consist of a high gloss, coated paper which is water-degradable or water-dispersible. Alternatively, the exterior layer 30 could have different finishes, such as semi-gloss or a satin finish. The coating on the first member 22 can be selected from a wide variety of materials. Some specific coatings include polyethylene, polypropylene, polyvinylidene chloride and polychloride alcohol. The exterior layer 30 can also be lubricated or contain an additive if desired. Suitable lubricants and additives include any of the pharmaceutically accepted lubricants or additives conventionally used in tampon applicators. Such lubricants and additives include organic compounds, long change aliphatic groups, such as derivatives of fatty acids, for example, stearamides and oleamides.

Paper used in the construction of the tampon applicator 10 should have a board weight per layer of from between about 20 pounds to about 200 pounds per ream, preferably, between about 25 pounds to about 100 pounds per ream, and most preferably, from about 30 pounds to about 50 pounds per ream. A "ream" is defined as material having dimensions of 24 inches (609.6 mm) by 36 inches (914.4 mm) by 500 sheets. Each paperboard layer should have a thickness of less than about 0.4 mm, preferably from about 0.04 mm to about 0.2 mm and, most preferably, from about 0.05 mm to about 0.16 mm. Normally, the exterior layer will be thinner than the interior paperboard layer(s).

If one of the layers 30 or 32 is made from a thermoplastic film, it can be polyethylene. A polyethylene film having high slip characteristics and a low density works well. The thermoplastic film should be thin, less than about 0.1 mm, preferably about 0.010 mm to about 0.050 mm, and most preferably about 0.012 mm to about 0.040 mm. Other kinds of films can also be used. Such films include cellulose ether selected from the group of aliphatic and aromatic ethers; films having ethylcellulose as the essential base constituent, or films of methyl cellulose; flexible, highly plasticized cellulose acetate, formate and similar other alkyl esters; vinyl vinylidene chloride or rubber hydrochloride, as for example, Pliofilm®, or vinylite resin.

The thermoplastic film can be clear or opaque. The film may run the entire length of the first member 22 or only extend along a portion thereof. The film can be on the exterior surface of the first member 22 or be one of the inner layers.

The layers 30 and 32 of the first member 22 can be held together by an adhesive, such as glue, or by heat, pressure, ultrasonics, etc. The adhesive can be either water-soluble or water-insoluble. A water-soluble adhesive is preferred for environmental reasons in that the first member 22 will quickly break apart when it is immersed in water. Such immersion will occur should the first member 22 be disposed of by flushing it down a toilet. Exposure of the first member 22 to a municipal's waste treatment plant, wherein soaking in water, interaction with chemicals and agitation all occur, will cause the layers 30 and 32 to break up in a relatively short period of time.

The first member 22 is sized and configured to house the absorbent tampon 12. The inside diameter of the first member 22 is sized to accommodate typical size tampons 12. Usually, the inside diameter of the first member 22 is less than about 0.75 inches (about 19 mm) and preferably less than about 0.625 inches (about 16 mm). Although the exterior diameter of tampons do vary, most tampons utilized by women have an external diameter of less than about 0.75 inches (about 19 mm). However, if one desired to use the applicator 10 to administer medication to an animal, such as a farm animal, larger size tampons 12 could be used.

The first member 22 should have a substantially smooth exterior surface which will facilitate insertion of the tampon applicator 10 into a woman's vagina. When the surface of the exterior layer 30 is smooth and/or slippery, the first member 22 will easily slide into a woman's vagina without subjecting the internal tissues of the woman's vagina to abrasion. The first member 22 can be coated to give it a high slip characteristic. Wax, polyethylene, a combination of wax and polyethylene, cellophane and clay are representative coatings that can be applied to the exterior layer 30 to facilitate comfortable insertion. The first member 22 can be a straight, elongated cylindrical tube formed on a central longitudinal axis. It is also possible to form the first member 22 into an arcuate shape. The arcuate or curved shape can assist in providing comfort when inserting the first member 22 into a woman's vagina. With a curved tampon applicator, it is possible to employ a curved tampon which again may be more comfortable for some women to use since the shape of the tampon may better fit the curvature of a woman's vagina.

Integrally formed on the first end 26 of the first member 22 and extending outwardly therefrom is an insertion tip 34. The insertion tip 34 is designed to facilitate insertion of the first member 22 into a woman's vagina in a comfortable manner. The insertion tip 34 should be made of a thin, flexible material or membrane which resists rapid absorption of vaginal fluid during the period of insertion of the tampon applicator 10 into the woman's vagina. The insertion tip 34 can be constructed of paper, paperboard or film material. When the first member 22 has only two layers, the insertion tip 34 should be formed out of the layer having the lower board weight. The lower board weight layer is normally the thinner layer. A film material is preferred because it is thin, soft and flexible. Suitable materials for the insertion tip 34 include a thin bonded nonwoven fabric layer coated with low density polyethylene, plasticized polyvinyl chloride or polyurethane. The insertion tip 34 can also contain a coating or impregnation which inhibits any substantial absorption of vaginal fluids. The coating may be an oil, a wax, or an acceptable organic compound. Alternatively, the insertion tip 34 can be self-lubricating. Such materials can be made of a polymer which inherently provides the outer surface with a low coefficient of friction. Typical polymers of this type are fluorinated, such as polytetrafluoroethylene (PTFE), fluorinated ethylene-propylene (FEP) and polyethyleneoxide (PEO).

The insertion tip 34 should have an outside diameter which is approximately equal to or less than the outside diameter of the first member 22. It should be noticed that when the diameter is less than that of the first member, the difference should be small so that the end of the exterior layer 30 cannot be felt by the woman during insertion. In FIGS. 1–3, the insertion tip 34 has a diameter which is less than the diameter of the first member 22. The insertion tip 34 can be configured to be rounded, semi-spherical or frustoconical. Other nose or dome-like shapes can also be utilized. The rounded configuration of the insertion tip 34 functions to prevent the forward end of the tampon 12 from exerting an abrasive action upon the wall of the vagina as would be the case if it was uncovered.

The insertion tip 34 is formed from at least one of the layers 30 and 32 which form the first member 22 and can be formed from more than one layer if desired, provided it has less thickness. The insertion tip 34 can be formed from at least one less layer than the number of layers from which the first member 22 is constructed. The insertion tip 34 has a thickness which is less than the thickness of the first member 22 so as to assure that it is soft and flexible. The thickness of the insertion tip 34 should be less than about 50% of the thickness of the first member 22, preferably less than about 75% of the thickness of the first member, and most preferably, less than about 80% of the thickness of the first member.

In FIGS. 1–3, the insertion tip 34 is shown having a plurality of soft and flexible petals 36 which are arranged to form a dome-shaped nose. The petals 36 are separated by narrow slots 38. The petals 36 are capable of radially flexing or bending outward to provide an enlarged opening through which the tampon 12 can exit when it is pushed forward by the second member 24. Either an even or an odd number of petals 36 can be used but preferably, there are an odd number of petals 36, such as 3, 5, 7, etc. because an odd number of petals 36 will prevent the first member 22 from collapsing or flattening after the tampon 12 has been expelled. By preventing the first member 22 from collapsing, one can be assured that the vaginal tissue will not be pinched when the tampon applicator 10 is removed from the user's vagina. For optimum performance, the insertion tip 34 will contain five petals 36, each having an elongated, approximately truncated shape with a rounded end and each being about 7/16 of an inch (about 11.1 mm) in length.

As stated above, the tampon applicator 10 includes a second member 24, also commonly referred to as an inner tube. The second member 24, like the first member 22, can be a spirally wound, convolutely wound or longitudinally seamed, hollow tube constructed from paper, paperboard, cardboard, plastic, film, aqueous coating or a combination thereof. The second member 24 can also be formed into a hollow tube by overlapping the material upon itself. The second member 24 can be constructed of the same material as the first member 22 or it can be made out of a different material. Furthermore, the second member 24 could be constructed as a laminate having two or more plies which are then spirally wound, convolutely wound or longitudinally seamed into a cylindrical tube. Either a wound tube or a longitudinally seamed tube is preferred because the finished tube will have a wall 40 with a constant thickness. However, some manufacturers may prefer to construct the second member 24 as a solid stick or use some other unique shape. The second member 24 also has a distal or free end 42 onto which the user's forefinger can rest for facilitating movement of the second member 24 into the first member 22. The distal end 42 thereby functions as a seat for the forefinger. It is also possible to form an enlarged ring or flange (not shown) on the distal end 42 of the second member 24 to provide for a larger contact surface.

The second member 24 functions by telescopically moving relative to the first member 22. As the second member 24 is pushed the first member 22, the tampon 12 is forced forward against the insertion tip 34. The contact by the tampon 12 causes the petals 36 to radially open to a diameter which is sufficient to allow the tampon 12 to be expelled from the first member 22. With the tampon 12 properly positioned in the woman's vagina, the tampon applicator 10 is withdrawn and discarded.

Figures 4, 5:
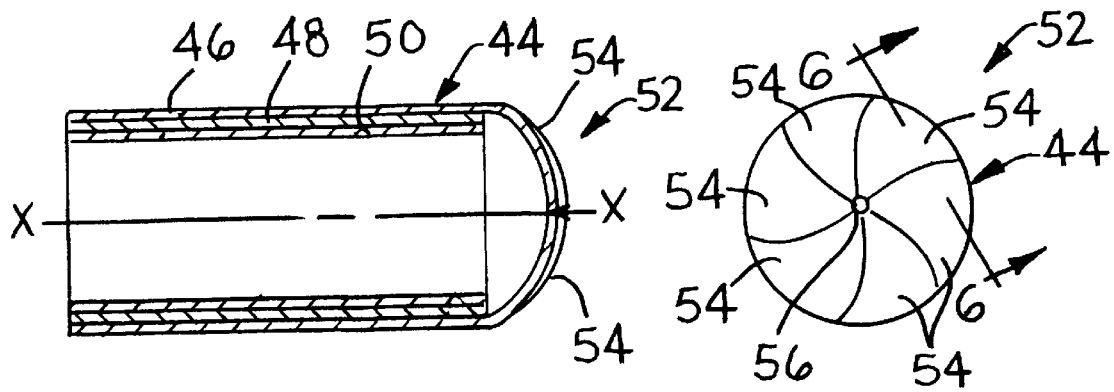
FIG. 4 is a cross-sectional view of an alternative embodiment of an outer tube constructed of three distinct layers and showing the insertion tip being formed from the outer layer.
FIG. 5 is a right end view of FIG. 4 showing the insertion tip formed with a plurality of soft and flexible pleats.
Figure 6:
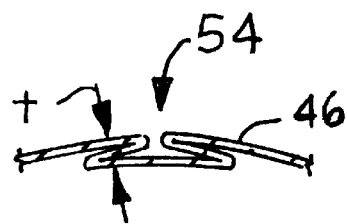
FIG. 6 is a schematic view of a pleat taken along line 6—6 of FIG. 5 depicting the shape and thickness of a pleat.

Referring to FIGS. 4–6, an alternative embodiment of a first member 44 is depicted which is formed along a central longitudinal axis X—X. The first member 44 can be constructed from paperboard, paper, cardboard, plastic, film or a combination thereof. The first member 44 is similar to the first member 22 except for two noticeable differences. The first difference is that the first member is formed from three layers 46, 48 and 50 instead of two layers. Layer 46 is the exterior layer and it can be coated to give it a smooth or slippery surface to facilitate comfortable insertion into a woman's vagina. The exterior layer 46 can alternatively be constructed from a very thin film having a thickness of about 0.001 mm. It should be noted that in FIGS. 4 and 6, the exterior layer 46 is depicted thicker than it needs to be simply for the purpose of illustration. The middle layer 48 can be constructed from any of the materials mentioned above and normally has a relatively high board weight. The middle layer 48 can be the thickest layer if desired. The inner layer 50 can be formed from a material having a higher board weight than the exterior layer 46 but should be relatively smooth to enable the second member 24 to telescopically slide thereon. The second difference is that the first member 44 has an outward extending insertion tip 52 formed with a plurality of flexible pleats 54. The plurality of radiating pleats 54 can have apices which terminate at or adjacent to the center forward end of the insertion tip 52. The pleats 54, of which there are six, although any number greater than three can be present, are arranged in an approximately semi-spherical configuration to form a dome shaped enclosure with an apex aligned with the central longitudinal axis X—X. The pleats 54 are capable of expanding radially outward as the tampon 12 is expelled from the first member 44 by movement of the second member 24 therein. The pleats 54 can totally enclose the forward end of the first member 44 or there can be an axially opening 56 formed at the apex of the pleats 54. When opening 56 is present, it should have a diameter of less than about 0.125 inches (3.175 mm).

Referring to FIG. 6, a schematic view of a pleat 54 is shown. The pleat 54 is obtained by folding the material upon itself so that when the pleat 54 is opened or unfolded it will occupy a much larger surface area. The thickness of the material forming the insertion tip 52 will be less than the thickness of the first member 44. The insertion tip 52 can have a thickness of between about 0.03 mm to about 0.5 mm. In the folded condition, the pleat 54 has a thickness, indicated by the letter "t" which should be less than about 1.0 mm, preferably between about 0.25 mm to about 0.35 mm.

Figure 7:
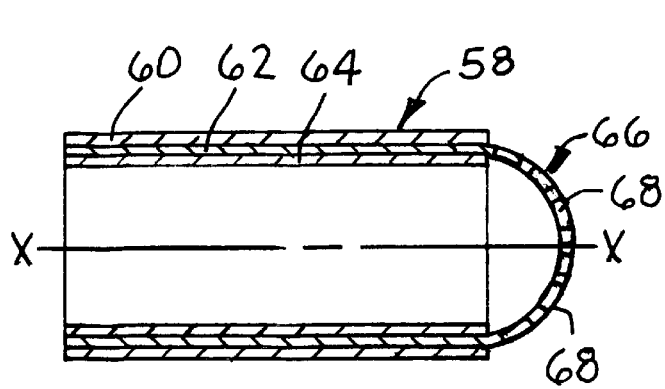
FIG. 7 is a cross-sectional view of another embodiment of an outer tube constructed of three distinct layers and showing the insertion tip being formed from the middle layer.
Figure 8:
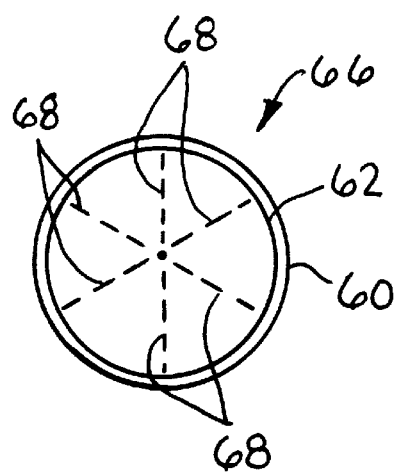
FIG. 8 is a right end view of FIG. 7 showing the insertion tip formed with a plurality of perforations.

Referring to FIGS. 7 and 8, a third embodiment of a first member 58 is shown which is constructed of three separate and distinct layers 60, 62 and 64. The outer or exterior layer is 60, the middle layer is 62 and the inner most layer is 64. An insertion tip 66 is integrally formed on the first member 58 and can have a semi-spherical, frusto-conical or dome like configuration with an apex aligned along the central longitudinal axis X—X of the first member 58, central longitudinal axis X—X. The insertion tip 66 differs from the embodiment shown in FIGS. 4–6 in two noticeable ways. First, the insertion tip 66 is formed from the middle layer 62 instead of from the exterior layer. In this case, the middle layer 62 can be a thin film while the other two layers 60 and 64 are formed from paper, paperboard or cardboard. The second difference is that the insertion tip 66 includes a plurality of perforations 68, instead of pleats. The perforations 68 extend from the apex of the insertion tip back toward the first member 58. In FIG. 8, six perforations 68 are shown but it should be recognized that any number of perforations can be present. Preferably, the perforations 68 can range from between two to twenty with a number between four and twelve being preferred. The perforations 68 can be present in either an even or an odd number and be located either an equal distance apart or at non-equal distances. The perforations 68 should be frangible and easily broken. The perforations 68 can be formed either on the inside or outside surface of the insertion tip 66. When the perforations 68 are formed on the inside surface of the insertion tip 66, a smoother surface is present on the forward end of the tampon applicator 10 which will facilitate a more comfortable insertion into a woman's vagina.

Figure 9:
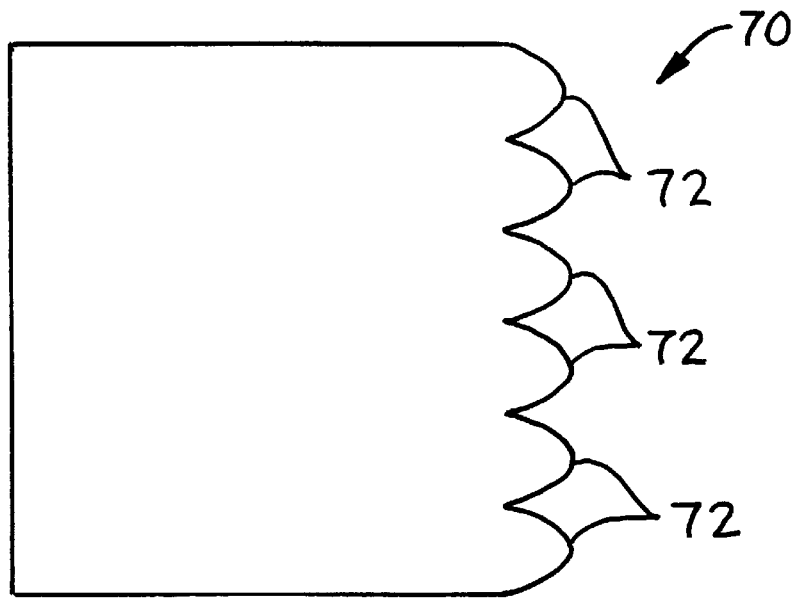
FIG. 9 is a plan view of a laminate sheet from which the outer tube can be formed.
Figure 10:
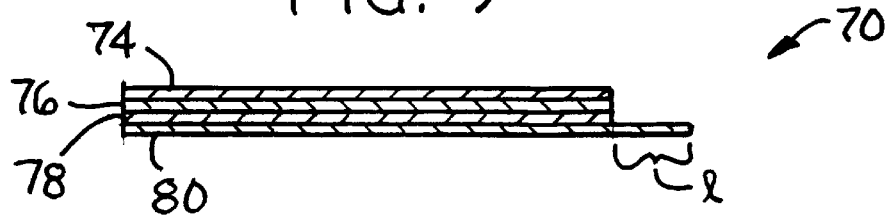
FIG. 10 is a side view of the laminate shown in FIG. 9 depicting the length and thickness of the various layers.

Referring to FIGS. 9 and 10, a laminate 70 is depicted having a plurality of scallops 72 formed along an edge thereof. The scallops 72 provide a series of approximately semi-circular, curved projections forming an ornamental border which can form multiple petals 36 on one end of a tubular member when the laminate is rolled into a hollow tube. This represents one method of forming the first member or outer tube of the tampon applicator 10. In FIG. 10, the laminate 70 is shown being constructed of four separate and distinct layers 74, 76, 78 and 80. The layers can be glued together or bonded in some other fashion known to those skilled in the art. The lower or exterior layer 80 has a length "1" which is longer than the other layers 74, 76 and 78. This extra length provides a location in which the scallops 72 can be formed. The longer length of the exterior layer 80 allows the laminate 70 to be rolled up into a hollow tube such that only the thickness of layer 80 will form the petals. The laminate 70 can be longitudinally seamed into a tubular configuration. This assures that the petals will be soft and flexible relative to the first member. The first member requires a certain amount of stiffness and rigidity in order to perform its function of delivering the tampon 12 into the woman's vagina.

It should be noted that if the first member 22, 44 or 58 is spirally or convolutely wound into a hollow, cylindrical shape, that the petals 36 may have to be cut out after the tube is formed. It should also be noted that it is possible to razor cut the inner layers of the first member adjacent to the first end 26 so that the insertion tip 34 is thinner than the thickness of the first member 22. This operation will allow the insertion tip 34 to be formed from a portion of two layers instead of just from a single layer.

Lastly, the tampon applicator 10 can be packaged within a sanitary pack if desired. A plastic or paper pouch can be used which can be made sterile by conventional sterilizing methods. Such sterilizing methods include gamma or electron irradiation, ethylene oxide gas or steam autoclaving. The use of such a sterile device can reduce the chance of causing an infection in the body cavity by insertion of the tampon 12 therein.

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

We claim:

1. A tampon applicator comprising:
   a) a straight, elongated cylindrical tube capable of housing an absorbent tampon, said tube having an outside diameter and first and second spaced apart ends, said tube being formed from at least two distinct layers which extend between said first and second ends, said layers including at least one interior layer and an exterior layer with one of said interior layers being a film;
   b) a flexible insertion tip integrally formed on said elongated cylindrical tube from said film layer, said flexible insertion tip extending outward from said first end and having a thickness which is less than that of said tube and said flexible tip having an outside diameter which is equal to or less than said outside diameter of said cylindrical tube; and
   c) a second member telescopically mounted in said second end of said elongated cylindrical tube, said second member adapted to expel said tampon through said flexible insertion tip as it is pushed into said tube.

2. The tampon applicator of claim 1 wherein said insertion tip has a thickness of less than about 50% of the thickness of said straight, elongated cylindrical tube.

3. The tampon applicator of claim 1 wherein said insertion tip has a thickness of less than about 75% of the thickness of said straight, elongated cylindrical tube.

4. The tampon applicator of claim 1 wherein said insertion tip has a thickness of less than about 80% of the thickness of said straight, elongated cylindrical tube.

5. The tampon applicator of claim 1 wherein said insertion tip includes a plurality of pleats arranged to form a semispherical configuration.

6. The tampon applicator of claim 5 wherein said pleats are capable of expanding radially outward as said tampon is expelled from said straight, elongated cylindrical tube.

7. The tampon applicator of claim 1 wherein said insertion tip includes a plurality of flexible petals.

8. The tampon applicator of claim 7 wherein said insertion tip includes an odd number of flexible petals.

9. The tampon applicator of claim 1 wherein said elongated cylindrical tube has a central longitudinal axis and said insertion tip has an apex aligned with said central longitudinal axis and a plurality of perforations extending from such apex toward said first end of said elongated cylindrical tube.

10. A tampon applicator comprising:
  a) a straight, elongated cylindrical tube capable of housing an absorbent tampon, said tube having an outside diameter and first and second spaced apart ends, and said tube being formed from at least two distinct layers which extend between said first and second ends, and each layer being formed from a different material, said layers including at least one interior layer and an exterior layer with one of said interior layers being a film;
  b) a flexible insertion tip integrally formed on said elongated cylindrical tube from said interior film layer, said flexible insertion tip extending outward from said first end and having a thickness which is less than that of said tube and said flexible tip having an outside diameter which is equal to or less than said outside diameter of said cylindrical tube; and
  c) a second member telescopically mounted in said second end of said elongated cylindrical tube, said second member adapted to expel said tampon through said flexible insertion tip as it is pushed into said tube.

11. The tampon applicator of claim 10 wherein said elongated cylindrical tube has a film layer having a thickness of between about 0.012 mm to about 0.040 mm.

12. The tampon applicator of claim 10 wherein said elongated cylindrical tube contains a film layer and two layers of paper.

13. A combination tampon and tampon applicator comprising:
  a) an absorbent tampon for insertion into a vagina, said tampon having withdrawal means secured thereto;
  b) a straight, elongated cylindrical tube capable of housing said absorbent tampon, said tube having an outside diameter and first and second spaced apart ends, said elongated cylindrical tube being formed from at least two distinct layers formed from two different materials, said layers including at least one interior layer and an exterior layer with one of said interior layers being a film, and at least two of said layers having a different weight;
  c) a flexible insertion tip integrally formed on said elongated cylindrical tube and extending outward from said first end, said flexible insertion tip being formed from said film layer and having a thickness which is less than that of said tube and said flexible tip having an outside diameter which is equal to or less than said outside diameter of said cylindrical tube; and
  d) a second member telescopically mounted in said second end of said elongated cylindrical tube, said second member adapted to expel said tampon through said insertion tip as it is pushed into said tube.

14. The combination tampon and tampon applicator of claim 13 wherein said elongated cylindrical tube includes an outer layer formed from paper.

15. The combination tampon and tampon applicator of claim 13 wherein said elongated cylindrical tube includes an inner layer formed from paper.

16. The combination tampon and tampon applicator of claim 13 wherein said cylindrical tube is formed from three layers and two of said layers are formed from paper.

17. The combination tampon and tampon applicator of claim 13 wherein said elongated cylindrical tube includes two paper layers of different board weight and a layer of film.

* * * * *